United States Patent [19]

Rosenwald

[11] Patent Number: 4,678,466
[45] Date of Patent: Jul. 7, 1987

[54] INTERNAL MEDICATION DELIVERY METHOD AND VEHICLE

[76] Inventor: Peter L. Rosenwald, 27 Broadview Rd., Cheshire, Conn. 06410

[21] Appl. No.: 815,295

[22] Filed: Dec. 27, 1985

Related U.S. Application Data

[63] Continuation of Ser. No. 673,661, Nov. 21, 1984, abandoned, which is a continuation-in-part of Ser. No. 277,188, Jun. 25, 1981, Pat. No. 4,484,922.

[51] Int. Cl.⁴ .............................................. A61K 9/22
[52] U.S. Cl. .................................. 604/891; 604/893; 604/285
[58] Field of Search .......................... 604/891–894, 604/285, 895

[56] References Cited

U.S. PATENT DOCUMENTS

| | | | |
|---|---|---|---|
| 2,962,023 | 11/1960 | Chappaz et al. | 604/285 |
| 3,995,635 | 12/1976 | Higuchi et al. | 604/893 |
| 4,111,202 | 9/1978 | Theeuwes | 604/894 |
| 4,249,531 | 2/1981 | Heller et al. | 604/891 |
| 4,450,150 | 5/1984 | Sidman | 604/891 |
| 4,484,922 | 11/1984 | Rosenwald | 604/891 |

Primary Examiner—John D. Yasko
Attorney, Agent, or Firm—Mattern, Ware, Stoltz & Fressola

[57] ABSTRACT

By providing an implantable insert incorporating a reservoir in which a therapeutic medication is stored, with said insert having a construction through which the medication is dispensed, a medication delivery vehicle is obtained which is capable of being inserted directly adjacent various organs in order to provide requisite medications directly to the organ. In the preferred embodiment, the medication delivery vehicle of this invention comprises a truncated conical shape, thereby allowing the delivery vehicle to be inserted into channel-like orifices, conduits, or vessels leading to the particular organ to which medication delivery is sought, without interfering with the normal bodily functions or the passage of fluids through the channel-like areas and without further movement from the site of implantation. In another embodiment, the delivery vehicle comprises a frusto-spherical annular shape for being inserted on the eye in circumscribing relationship with the corneal-scleral junction, without intruding upon that junction. In this way, medication is delivered directly to the cornea of the eye.

10 Claims, 9 Drawing Figures

INTERNAL MEDICATION DELIVERY METHOD AND VEHICLE

RELATED APPLICATION

This application is a continuation of application Ser. No. 673,661 filed Nov. 21, 1984 now abandoned which is a continuation-in-part of my co-pending application, bearing Ser. No. 277,188, filed June 25, 1981 now U.S. Pat. No. 4,484,922.

TECHNICAL FIELD

This invention relates to medication delivery vehicles for dispensing therapeutic medications directly to specific organs in the human body, without interfering with otherwise normal physical operation of the body.

BACKGROUND ART

There has long been a need for delivery of medication to specific organs or areas of the body in order to dispense medications directly at the site of an injury or diseased area, without having the medication dispensed throughout the entire body. Unfortunately, an effective delivery vehicle of this nature has heretofore been unobtainable.

In general, prior art medication delivery is most often achieved by ingesting the medication, requiring the medication to circulate throughout the bloodstream in order to distribute the medication to the desired area. Unfortunately, other parts of the body also receive the medication which, in many instances, causes adverse side effects.

Alternatively, prior art delivery systems have employed the use of injections to deliver necessary medication directly to the desired site. In addition to limited applicability, the use of injections is undesirable since large dosages of the medication must be absorbed by the body. In addition, the effect of the injection wears off after a period of time, usually requiring repeated follow-up injections. Consequently, the body is repeatedly exposed to peaks of large dosages of medication interspersed with long periods of little or no medications. As a result, these prior art systems are incapable of providing medication delivery at a reasonably constant controlled rate over an extended period of time.

In the treatment of eyes, both temporary and more permanent disorders have generally been handled by placing liquids, salves, or other medicaments directly in the eye by means of a squeeze tube or an eye dropper or by flushing the eye with a wash glass. More recently, however, delivery vehicles have been developed in which medication is confined within a small semipermeable body which is inserted under one of the eyelids. The medication is diffused from the body into the tear or lacrimal fluids in the eye and is dispersed over portions of the eye and surrounding areas by the lacrimal fluids.

One form of delivery vehicle inserted into the eye is known as a "soft contact lens". Soft contact lenses consist of a highly porous plastic which can absorb water or other fluids up to 74 percent of its volume. By soaking such a lens in a fluid medication and inserting the lens in the eye in conventional fashion, a dosage of the medication is distributed in the eye by the lacrimal fluids.

Certain difficulties arise with treatment by means of soft contact lenses. While they absorb a substantial quantity of medication, the plastic material of which they are comprised cannot control the release rate of the medication and as a consequence, strong doses of the medication are dispensed in the eye initially and weak doses after a protracted period. Such variations in the dispensing rate resemble the treatment obtained by periodic applications of medication from an eye dropper and is not the most effective method of treating chronic or more persistent disorders such as glaucoma. Initial doses are strong and lose their effectiveness after a certain period of time. The effects of the medication can be extended by increasing the initial concentration of drugs utilized in the medication; however, the danger of irritation from high toxicity limits such an approach. Additionally, a soft contact lens, as any contact lens, blocks the supply of oxygen to the cornea and, hence, continuous use of the lens for periods of more than twenty-four hours is not recommended. Interrupting treatment by removing the lens for rest periods aggravates the difficulty of providing a constant level of medication to the eye.

Another type of delivery vehicle which has overcome many of the difficulties associated with soft contact lenses employs a body of polymeric plastic in which a reservoir of medication is held. The polymeric material can be designed to control the release rate of the medication and thus provide a more uniform level of medication within the eye for extended periods of time. U.S. Pat. Nos. 3,618,604 and 3,828,777 issued to Richard A. Ness disclose delivery vehicles of this type in detail. In practice, the body has a small ellipsoid or bean shape and is inserted in the conjunctival sac between the sclera and one of the eyelids. The medication diffuses through the polymeric material to the surface of the device and is spread over the surface of the eyeball by the lacrimal fluids. The great benefit obtained by these devices is the controlled rate at which the medication is released from the device by the polymeric material. The medication reaches the eye at a relatively uniform rate compared with soft contact lenses and the supply of medication in the device is not immediately expended but, instead, is dispensed gradually over a protracted period of time.

However, one difficulty which arises from these prior art devices inserted in the eye is caused by the sensitivity of the eye to foreign bodies which make contact with the eye, especially in the corneal region. A foreign body can become a source of irritation to the patient which renders the use of an insert impractical and offensive unless it is held in an area of low sensitivity. Irritation stimulates defense mechanisms which protect the eye against foreign objects. The lacrimal glands become more active and produce tearing to wash the object from the eye. Even if tearing is unsuccessful in dislodging an insert, the tear fluids act as a diluent to the dispensed medication and also leach further medication from the delivery vehicle. Excess tearing results in overflow of the conjunctival sacs and, as a result, the medication itself is washed out of the eye in tears.

Another reaction of the eye which aggravates the retention problem is the increased eye mobility caused by local irritation. The eyeball tends to move up and down while the lids open and close in order to expel a foreign object. Even if an insert is not expelled from the eye by these reactions, it can be dislodged to a point where it contacts a highly sensitive area, such as the cornea. In most patients, contact with the cornea cannot be tolerated even momentarily and the eye defense mechanisms are brought immediately to a highly active state which usually results in expulsion of the foreign body.

In addition to the prior art inability to provide comfortable, trouble-free delivery of medication to the eye, many other areas of the body need the direct delivery of medication at a controlled rate over an extended period of time, but have not been able to obtain such medication delivery. In particular, organs such as the liver, spleen, pancreas, heart, lungs, stomach, etc. could benefit from a delivery vehicle of this nature, as well as other areas such as the nasal passages, salivary glands, esophagus, trachea, pharynx, eustachian tube, blood vessels, etc.

In addition, the controlled delivery of cancer drugs directly to the cancer site would be extremely beneficial. However, no such prior art delivery vehicle has been developed.

Therefore, it is a principal of the present invention to provide a medication delivery vehicle which provides a slow, controlled release of medication over an extended period of time, without interfering in any way with normal bodily functions.

Another object of the present invention is to provide a medication deliver vehicle having the characteristic features described above, which can be surgically inserted or directly implanted in close proximity to the particular organ or site for which medication is required.

Another object of the present invention is to provide a medication delivery vehicle having the characteristic features described above, which is capable of delivering desired medication to a particular site or organ without adversely affecting the entire body, avoiding medication delivery through th entire body by the body's circulatory system.

Other and more specific objects will in part be obvious and will in part appear hereinafter.

SUMMARY OF THE INVENTION

The present invention attains a universally applicable medication delivery vehicle which dispenses therapeutic medication to any particular site or organ at a controlled rate over an extended period of time. The delivery vehicle of the present invention can be utilized to treat a broad range of chronic, as well as temporary diseases.

In its preferred embodiment, the medication delivery vehicle of the present invention comprises a truncated conical shaped member which is either surgically inserted or manually implanted directly adjacent the particular organ or site at which medication is required. Generally, any channel-like passageway, vessels, or other elongated open zone or orifice can accommodate the medication delivery vehicle of this invention.

In view of the truncated conical shape preferably employed by the delivery vehicle of this invention, the normal bodily function through the particular channel-like, passageway, or orifice continues without any degradation or adverse effects. In addition, the truncated conical shape of the delivery vehicle of this invention assures secure retainment of the delivery vehicle in the precise, implanted position, while the body operates in its normal manner.

In the preferred construction, the truncated conical medication delivery vehicle of this invention comprises polymeric material through which medication diffuses at a controlled rate into the normal fluid passing through the channel in which the delivery vehicle is placed.

In the embodiment used on the eye, the delivery vehicle is utilized to treat chronic diseases such as glaucoma by dispensing a drug such as pilocarpine at a relatively uniform rate for an extended time period. In this embodiment, the delivery vehicle is comprised of a body made from a non-allergenic material, insoluble in lacrimal fluids and containing a known quantity of therapeutic medication in a particular concentration. Preferably, the material from which the body is formed is a polymeric material through which the medication diffuses into the lacrimal fluids of the eye for uniform dispersion over the eye and distribution into adjacent regions.

It is an important feature of this embodiment of the present invention that the body have a generally annular shape with a size sufficient to allow placement of the delivery vehicle on a less sensitive area of the eye in circumscribing relationship with the corneal-scleral junction without intruding upon this more sensitive junction. In this embodiment, the body extends over the surface of the eyeball away from the junction into the upper and lower conjunctival sacs under the upper and lower eyelids respectively. The eyelids and eye curvatures aid in retaining the delivery vehicle in place and thus supplement the capillary action generated by the lacrimal film between the delivery vehicle and the eyeball.

By sizing the body so that it circumscribes the corneal-scleral junction, the cornea is exposed in a natural manner. More importantly, the foreign-body awareness and retention problems experienced with the prior art inserts are reduced since the insert of the present invention is held in place by the eyelids and the compound curvatures of the eyeball in the region around the corneal-scleral junction In another embodiment, the medication delivery vehicle of this invention is utilized to treat chronic asthmatics by dispensing a drug such as Theodor at a relatively uniform rate over an extended period of time directly to the lungs of the asthmatic. In this embodiment, the medication delivery vehicle comprises a truncated conical shape and is inserted directly in the trachea in order to allow the medication to be delivered directly to the bronchial tubes and the lungs. In this embodiment, the medication is dispensed from the delivery vehicle, both by gravity and by the movement of air into the lungs by normal breathing.

In alternate embodiments, the medication delivery vehicle of the present invention with its generally truncated conical shape can be employed in the nasal passages, air canals, salivary glands, esophagus, eustachian tubes or pharynx. In addition, the delivery vehicle of this invention can be inserted in the arteries or veins, in order to deliver medication directly to the heart, or other organs in the circulatory system, such as the liver, spleen, pancreas, etc. In addition, the digestive system can have medication delivered to organs such as the stomach, duodenum, colon, or directly to the rectum. Furthermore, urinary organs, as well as male and female organs of generation can have medication delivered to necessary areas using the delivery vehicle of this invention.

The invention accordingly comprises the steps and the relation of one or more of such steps with respect to each of the others and the apparatus employing features of construction, combination of elements and arrangement of parts which are adapted to effect such steps, all as exemplified in the following detailed disclosure and the scope of the invention will be indicated in the claims.

THE DRAWINGS

For a fuller understanding of the nature and objects of the invention, reference should be had to the following detailed description taken in connection with the accompanying drawings in which.

DETAILED DESCRIPTION

Figure 1:
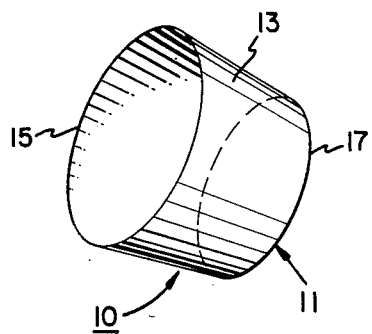
FIG. 1 is a perspective view of the preferred embodiment of the medication delivery vehicle of the present invention.

In FIG. 1, medication delivery vehicle 10 is depicted in its preferred embodiment comprising a substantially truncated conical shaped member 11. Member 11 comprises a wall portion 13 in which the desired medication is retained for subsequent dispensing directly to the desired site. Conical shaped wall 13 terminates at one end with a first, substantially circular-shaped edge 15, and at the opposed and in a second, substantially concentrically aligned circular-shaped portal-defining edge 17.

Member 11 and its truncated conical shaped wall portion 13 incorporates a quantity of therapeutic medication contained directly within wall portion 13. Medication may be contained in either a single compartment reservoir within wall portion 13 or can be distributed in a finely divided manner in porous material defining multiple interconnected reservoirs. One material which is employed to form wall portion 13 is an imperforate polymeric material such as described in U.S. Pat. No. 3,618,604 or a microporous polymeric material in which the pores are filled with a liquid or gel medium for controlling the release rate of medication as described in U.S. Pat. No. 3,828,777. For more detailed description of such materials and their structures, reference should be made to the cited patents.

In the preferred embodiment, medication delivery vehicle 10 comprises an overall size and shape dimensioned to fit the particular channel-like conduit, opening, vessel, or orifice which is directly adjacent the desired organ or site at which the medication is desired. In general, the diameter of edges 15 and 16 are constructed to comprise the precise size for the area in which delivery vehicle 10 is to be securely implanted. Although specific dimensions are detailed below, the particular configurations are provided merely for exemplary purposes, and not in any way to limit the scope of this invention.

Regardless of the particular diameter of concentrically aligned portal-defining edges 15 and 17, as well as the resulting angular slope at which sidewalls 13 is provided, the preferred configuration for medication delivery vehicle 10 is a substantially truncated conical shape member 11. This configuration is preferred in order to allow direct surgical implantation or manual insertion of medication delivery vehicle 10 at the desired location, while also assuring that the medication delivery vehicle in no way impedes the normal bodily function or fluid flow through the conduit, opening, channel or orifice in which medication delivery vehicle 10 is positioned. Furthermore, it has been found that truncated conical shape member 11 also provides an inherently stable member which is quickly and easily retainingly embedded in the desired receiving channel-like zone, in a secure, fixed orientation, free from unwanted rolling, twisting, or dislodgement.

Figure 2:
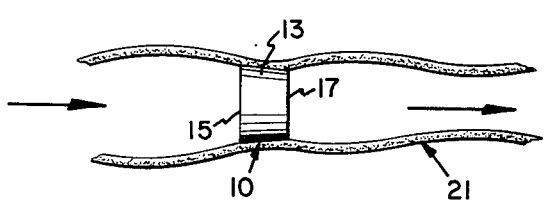
FIG. 2 is a schematic cross-sectional elevation view of the medication delivery vehicle of this invention positioned in a channel-like bodily conduit.

In FIG. 2, medication delivery vehicle 10 is depicted in an elongated, channel-like conduit 21. Conduit 21 is depicted as a general representation or any substantially cylindrical, elongated tubular-shaped fluid carrying member or vessel found throughout the body. Such fluid carrying member includes arteries, veins, the digestive tract, the colon, rectum, the ear canal and the trachea or windpipe.

As shown in FIG. 2, medication delivery vehicle 10 is securely embedded in tubular conduit 21, with the substantially truncated conical shaped wall portion 13 in direct abutting embedded engagement with conduit 21. Furthermore, the normal fluid passing through conduit 21 is not affected by delivery vehicle 10, since the fluid is free to flow through the portal defined by edges 17 and 15.

In the preferred embodiment, the larger diameter portal-defining edge 15 is positioned to receive the fluid flowing through conduit 21, while portal-defining edge 17 represents the exit portal as the fluid passes through medication delivery vehicle 10. Although medication delivery vehicle 10 can be arranged in the directly opposite manner, it has been found that by having the fluid flow through the larger diameter portal first, delivery vehicle 10 operates more efficiently, while providing further assurance that vehicle 10 is not in any way dislodged or moved from its embedded position.

If desired, medication delivery vehicle 10 may be constructed from a biodegradable or bioerodable material. One such bioerodable material is defined in U.S. Pat. No. 3,867,519. In this way, the removal of medication delivery vehicle 10 from its implanted position, such as a surgically implanted position, is not necessary, since medication delivery vehicle 10 will be degraded and carried away through normal bodily functions after the desired medication has been fully and completely dispensed.

In addition, medication delivery vehicle 10 may also comprise a composite structure with a drug impregnated matrix and an insoluble polymeric membrane as the outer skin thereof, in a general manner as defined in U.S. Pat. No. 3,854,480.

In FIGS. 3-6, medication delivery vehicle 10 of the present invention is depicted in its ophthalmic embodiment. In this embodiment, delivery vehicle 10 is inserted in the eye to dispense medication at a controlled rate for an extended period of time. For example, this delivery vehicle 10 may be used to treat chronic disorders such as glaucoma by continuously dispensing a drug such as pilocarpine at a controlled rate for a period up to a week without replacement.

In this embodiment, delivery vehicle 10 comprises a body 12 formed from a nonallergenic material which is insoluble in lacrimal or tear fluids. A quantity of therapeutic medication is confined within the body so that it may be diffused through the surface of the body into the lacrimal fluids when the body is placed on the surface of the eyeball.

Figure 3:
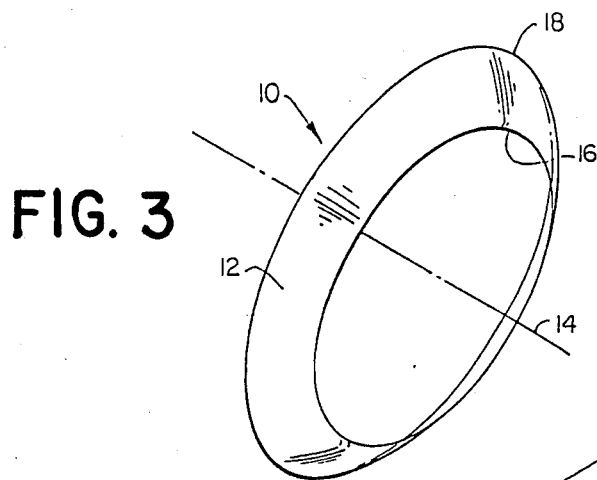
FIG. 3 is a perspective view illustrating an alternate embodiment of the delivery vehicle of the present invention.

As shown in FIG. 3, the body 12 has a generally annular shape. The walls of the body have a slight spherical curvature so that the body resembles the frustum of a sphere defined between two parallel planes perpendicular to the polar axis 14 of the sphere. Such a frustospherical, annular shape has a polar marginal edge 16 at the front or anterior portion of the body and an equatorial marginal edge 18 at the rear or posterior edge of the body. The diameter of the annular body is smallest at the polar marginal edge 16 and is largest at the equatorial marginal edge 18. The diameters and curvature of the body are selected to allow the body to be placed in the eye as shown in FIGS. 4–6.

Figure 4:
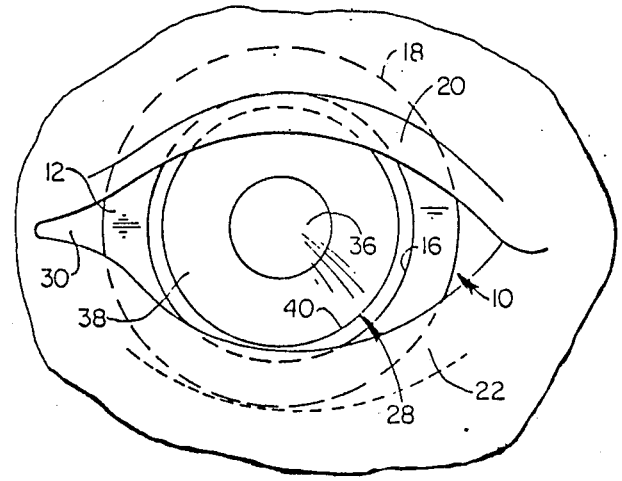
FIG. 4 is a front elevation view of the human eye showing placement of the delivery vehicle of FIG. 3.
Figure 5:
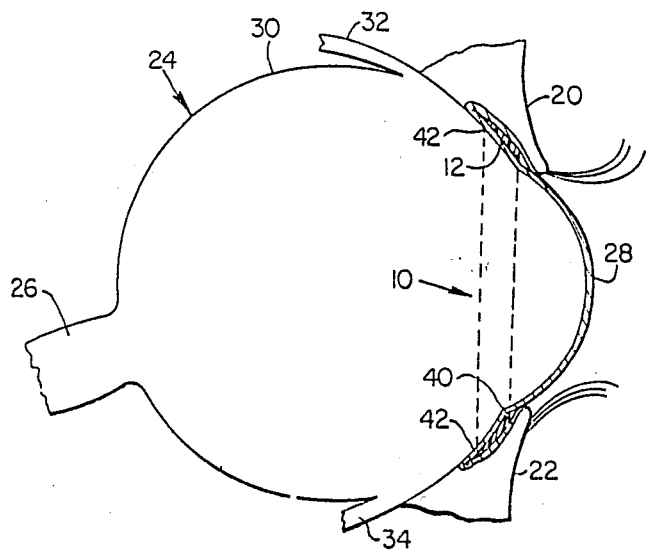
FIG. 5 is a sectional view of the human eye showing the delivery vehicle of FIG. 3 extending into the conjunctival sacs behind the upper and lower eyelids.
Figure 6:
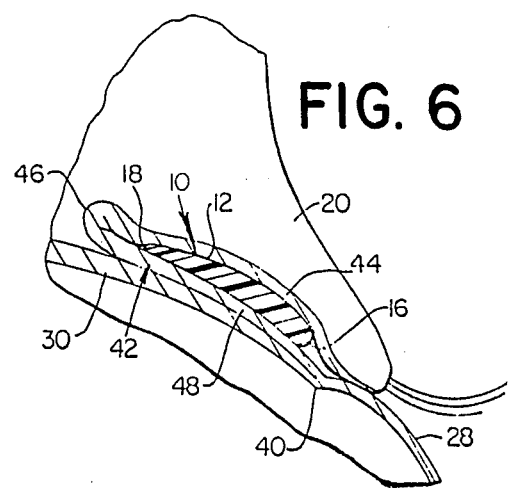
FIG. 6 is an enlarged sectional view of the eye and the delivery vehicle of FIG. 3 in the conjunctival sac behind the upper eyelid.

To more clearly understand this embodiment of the present invention, a brief description of the anatomy of the eye is provided in connection with FIGS. 4–6. The eye fits in a cavity of the skull known as the orbit and is exposed at the anterior portion by a palpebral opening or fissure defined by the upper eyelid 20 and lower eyelid 22. The globe 24 or eyeball connects at the posterior with the optic nerve 26 and is comprised of two merged, generally spherical sections, the anterior section being defined as the cornea 28 which is transparent and the posterior section being defined as the sclera 30 which is white and more commonly referred to as the white of the eye. The eye muscles 32 and 34 are attached to the sclera for moving the eye in its orbital socket.

The pupil 36 of the eye is an opening on the optical axis and is defined by the iris 38 or colored portion of the eye situated posteriorly of and visible through the transparent cornea 28.

As shown in FIGS. 5 and 6, the cornea 28 has a much smaller radius of curvature than the sclera 30. In actuality, neither the cornea nor the sclera are truly spherical but tend to flatten slightly as the distance from the optical axis increases. The curvature of the cornea differs from person to person, and hence is difficult to utilize as an interface with delivery vehicles such as soft contact lenses which ar placed directly on the cornea.

The junction of the sclera 30 and cornea 28 is identified as the limbus 40 and can be seen in the eye at the point where the white sclera joins the transparent cornea. The limbus, accordingly, defines the outer limit of the cornea which contains a high concentration of nerve endings serving to protect the cornea from dryness and injury from foreign objects. It is this cornealscleral junction that identifies the region in which ophthalmic delivery vehicles should not intrude; otherwise the natural protective systems of the eye attempt to work the delivery vehicle out of the eye.

The conjunctiva 42 is a thin mucous membrane that connects the inner side of the eyelids to the eyeball in the vicinity of the corneal-scleral junction or limbus 40. As seen in FIG. 4, the conjunctiva is a folded membrane having a palpebral portion 44 that connects with the margins of the eyelids and extends in the posterior direction to a fold or fornix 46 and a bulbar portion 48 which extends from the fornix in the anterior direction over the eyeball where it merges with the sclera and the cornea at the limbus 40. The conjunctiva 42 thus forms a circular cul-de-sac known as the conjunctival sac which surrounds the eyeball and prevents foreign objects from migrating rearwardly under the eyelids to areas within the orbit behind the eyeball. The conjunctiva also serves as a small reservoir for lacrimal fluids which are wiped across the cornea by blinking the eyelids as needed to prevent corneal dryness. In the presence of irritations in the eye and the secretion of excess lacrimal fluids, the conjunctival sac fills with fluids and overflows to form tears, initially at the nasal corner of the eyelids.

In this embodiment of the present invention, the delivery vehicle 10 is positioned on the globe of the eye coaxially of the optical axis and is sized so that it circumscribes the corneal-scleral junction 40 without intruding upon the junction. Thus, as illustrated in FIGS. 4 and 6, the polar marginal edge 16 of the body 12 has a diameter slightly larger than the diameter of the cornea 28. It is also common for the corneal-scleral junction to be flattened at the top and bottom edges so that it has a slightly elliptical shape with, for example, a horizontal dimension 12 mm and a vertical dimension of 11 mm. Preferably, body 12 of delivery vehicle 10 also has a slightly elliptical shape conforming to that of the junction. As a minimum, the inside diameter of the polar marginal edge should not be less than 11 mm to prevent intrusion onto the cornea 28.

The annular body 12 extends from the polar marginal edge 16 over the eyeball in the posterior direction with the upper and lower portions projecting into the conjunctival sacs behind the upper and lower eyelids 20 and 22. The curvature on the inner surface of the body between the marginal edges 16 and 18 is preferably matched with the curvature of the sclera in the region adjacent the limbus 40 so that the body lies flat on the bulbar portion 48 of the conjunctiva and remains in place due to the curvature and the capillary action developed by the film of lacrimal fluid on the eye and in the conjunctival sacs. The eyelids 20 and 22 overlie the exterior surface of the body 12 as shown most clearly in FIGS. 5 and 6 and develop additional forces for holding the body in place coaxially of the cornea 28. The degree to which the body 12 extends posteriorly behind the eyelids 20 and 22 depends partly upon the amount of semipermeable surface area needed to dispense medication in the eye. If the polar marginal edge 16 is spaced, for example, 1 mm from the cornea 28, then the diameter of the equatorial marginal edge 18 may be smaller than the corresponding diameter of a body which has the polar marginal edge 16 2 mm from the cornea, assuming the same dose rate is desired. It is contemplated, that the width of the annular body measured from the polar marginal edge to the equatorial marginal edge will in most cases be not more than 4 mm and will lie generally in the range of 2–4 mm. The thickness of the body from the interior surface contacting the bulbar portion 48 of the conjunctiva to the exterior surface contacting the palpebral portion 44 may also vary between 0.1 mm and 1 mm with a nominal dimension being 0.2 mm.

By employing this embodiment of delivery vehicle 10 in the eye, the lacrimal fluid and the blinking action of the eyelids carry medication diffused through the surface of the body over the eyeball and allow the medication to operate in the eye and surrounding regions. The body 12 is held firmly in position by capillary forces and the curvatures of the sclera in the region of the limbus 40. Thus, movement of the eyeball does not have a tendency to dislodge the body. The body is sized to remain outside of the highly sensitive corneal region to prevent irritation and also fully exposes the cornea in a natural manner to the eyelids and lacrimal fluids. Accordingly, the foreign-body awareness problem and the retention problems of the prior art devices are minimized, and with the cornea fully exposed, drying or oxygen depletion which occurs after prolonged wearing of a soft contact lens is avoided entirely.

Figure 7:
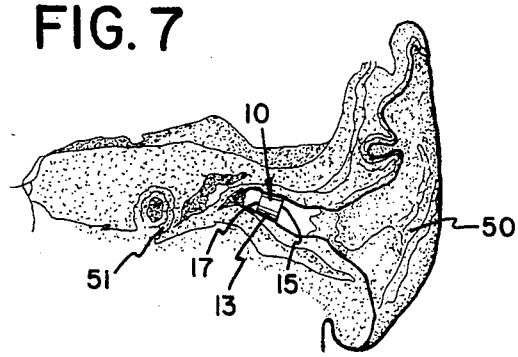
FIGS. 7-9 are cross-sectional elevation views of alternate embodiments of the medication delivery vehicle of this invention mounted in various other locations in the human body.

In FIG. 7, medication delivery vehicle 10 of the present invention is shown in an alternate implanted position. In this embodiment, medication delivery vehicle 10 is inserted directly into the auditory meatus or ear canal 50, in order to deliver medication directly to the inner ear. In this embodiment, medication delivery vehicle 10 is preferably constructed with a substantially truncated conical shape and securely embedded in ear canal 50, directly adjacent the membrane tempani 51, found near the end of the auditory meatus.

Since the auditory meatus comprises a substantially oval shaped, cylindrical canal composed of very flexible, fibrocartilage for the first one-third of an inch, delivery vehicle 10 may comprise one substantially uniform size for adults and another substantially uniform size for children. However, if desired, delivery vehicle 10 may be constructed with a specific, individualized size. Once implanted, gravity would cause the medication contained within delivery vehicle 10 to be slowly dispensed to the desired site, without any change or degradation in hearing being experienced by the user.

Figure 8:
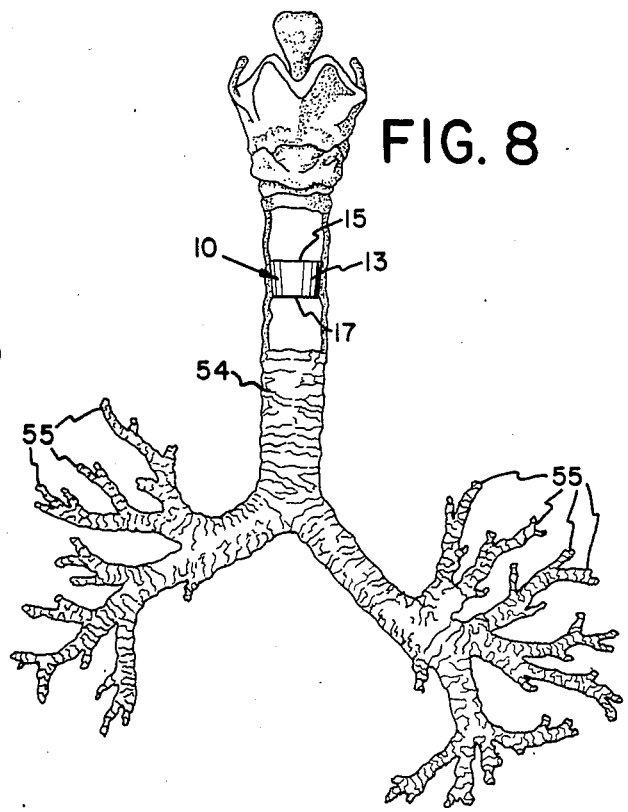

In FIG. 8, another alternate embodiment of medication delivery vehicle 10 is shown. In this embodiment, medication delivery vehicle 10 is inserted directly in the trachea 54 for delivering medication to bronchial tubes 55 and the lungs (not shown). Typically, such diseases as asthma could be efficiently and effectively treated by having medication delivered directly to these affected areas.

As shown in FIG. 8, medication delivery vehicle 10 is embedded directly in trachea 54, with wall portion 13 of medication delivery vehicle 10 in direct, abutting, secure engagement with the walls of trachea 54. In this way, the medication contained in the wall portion 13 of delivery vehicle 10 is dispensed at a controlled rate over an extended period of time, directly to bronchial tubes 55 and the lungs. In this embodiment, the medication is dispensed both by gravity as well as by the air flow through delivery vehicle 10 during normal breathing.

In this embodiment, medication delivery vehicle 10 is constructed in an overall configuration to assure secure, retained embedded engagement along the walls of trachea 54. The trachea, or windpipe, is a substantially cylindrical tube composed of cartilage and membrane. In general, the trachea is about four and one-half inches long, with an average diameter of about ⅝ inches. As a result, this embodiment of medication delivery vehicle 10 would incorporate the preferred, generally truncated conical shape, with larger diameter, portal defining edge 15 having a diameter of about ⅝ inches and with smaller diameter portal defining edge 17 having a diameter of about 9/16 inches. In addition, the vertical distance between edges 15 and 17 would preferably be between about one-quarter inches to about one inch.

Figure 9:
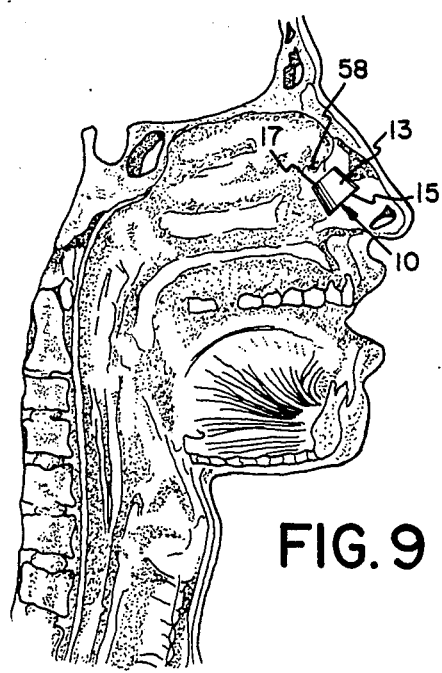

In FIG. 9, delivery vehicle 10 is depicted inserted in a nasal passageway 58, in order to dispense medication directly to the mucous membranes surrounding the nasal passageway. Wall portion 13 of delivery vehicle 10 is positioned in direct, abutting, secure engaged contact with the walls of nasal passageway 58, with the medication contained in wall portion 13 of delivery vehicle 10 ready to be dispensed at a controlled rate over an extended period of time directly to the desired site. In this embodiment, medication is dispensed by the air flowing through delivery vehicle 10 during normal breathing. In addition, medication delivery vehicle 10 is preferably constructed with a particular size dimensioned for the nasal passageways of the individual requiring the medication delivery.

Also shown in FIG. 9 is the pharynx, which is a musculo-membraneous tube located behind the nose, mouth and larynx. The pharynx is about four and one-half inches in length and represents another site in which medication delivery vehicle 10 of the present invention could be implanted.

As is readily apparent from the foregoing detailed disclosure and the examples of uses for the delivery vehicle of the present invention, medication delivery vehicle 10 of the present invention is capable of delivering any desired medication directly to any particular organ or site without causing potentially adverse effects from the medication circulating throughout the body, or in any way adversely affecting normal bodily functions. By providing a medication delivery vehicle having a generally truncated conical shape, the vehicle can be quickly and easily embedded or surgically implanted in any particular channel-like conduit, vessel, or cavity to deliver the desired medication to the precise location, without in any way adversely affecting the fluid flowing through the channel-like vessel or conduit. Furthermore, secure retained embedment in the desired position is provided while the desired medication is delivered at a controlled rate, over an extended period of time.

In an alternate embodiment, the medication delivery vehicle of the present invention may comprise an elongated, continuous, flexible, tape-like structure which can be wrapped around particular sites to which medication must be dispensed at a desired, controlled rate. In this embodiment, bones, muscles, tendons and subcutaneous sacs and joints for diseases such as arthritis are efficiently an effectively treated.

In this embodiment, the substantially continuous elongated length of membrane is constructed with the desired medication contained therein, and the membrane is wrapped about the bone, muscle or other affected area for allowing medication to be dispensed directly to the particular site where an injury or disease has been found. In this way, the advantages obtained by the medication delivery vehicle of the present invention are efficiently attained and the treatment of specific localized diseases are treated without adversely affecting the entire body.

It will thus be seen that the objects set forth above, among those made apparent from the preceding description, are efficiently attained, and since certain changes may be made in carrying out the above method or in the constructions set forth without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described my invention, what I claim as new and desire to secure by Letters Patent is:

1. A method for delivering medication directly to a particular desired organ or site, both comfortably and efficiently, comprising the steps of:
A. providing a thin walled, substantially continuous, non-allergenic, elongated, hollow body having a generally tubular shape with
   a. a first proximal edge comprising a generally rounded shape and defining a first portal zone,
   b. a second distal edge comprising a generally rounded shape and defining a second portal zone,
   c. a substantially continuous, elongated length of thin-wall material
      1. extending between and interconnecting said proximal edge with said distal edge,
      2. comprising an outer peripheral surface and an inner peripheral surface, and a total thickness therebetween of between about 0.1 millimeters and 1 millimeter, and
      3. defining an elongated substantially continuous fluid flow zone
         i. commencing at said first portal zone,
         ii. terminating at said second portal zone, and
         iii. peripherally surrounded and defined by said inner peripheral surface, and
   d. conduit-engaging and postion-anchoring means formed on the outer peripheral surface of said body;
B diffusing thereapeutic medication throughout the body for retention therein and subsequent delivery to the desired site; and
C. implanting the medication delivery vehicle in the desired fluid-carrying conduit with the conduit-engaging and position-anchoring reans thereof in secure, abutting locking engagement with the walls of the conduit, preventing unwanted movement of said vehicle, and with the continuous surface thereof being in aligned, cooperating relationship with said conduit,
whereby a medication delivery vehicle is attained which assures the delivery of medication directly to a particular desired organ or site, effectively and efficiently, delivering the medication directly to a particular site, without interfereing with normal fluid flow through the conduit, and which is securely lockingly engaged in the precisely desired position.

2. the method defined in claim 1, wherein said fluid is further defined as comprising a liquid.

3. A medication delivery vehicle comprising an elongated member
A having a substantially continuous, generally tubular shape, said tubular shape being formed and defined by a substantially continuous, thin-walled material having
   a. a first portal zone formed at a first end thereof,
   b. a second portal zone formed at the opposed end thereof, and
   c. a substantially continuous outer peripheral surface and a substantially continuous, juxtaposed, spaced, substantially aligned inner peripheral surface, with an overall depth therebetween of between about 0.1 millimeters and 1 millimeter;
B. being insertable into an elongated, continuous, generally cylindrically shaped fluid-carrying conduit of the human body with the central axis thereof being substantially coaxially aligned wtih the central axis of said fluid carrying conduit, and the outer peripheral surface of said thin-walled medication delivery vehicle being in substantially aligned, juxtaposed, relationship with the inner peripheral surface of the fluid carrying conduit, whereby said medication delivery vehicle is implantable in the fluid carrying conduit with said first and second portal zones thereof allowing fluid flow therethrough in a manner which prevents interference with the normal fluid flow of the conduit; and
C. further comprising conduit-engaging and position-anchoring means formed on the outer peripheral surface of said elongated member, positioned for secure, abutting and locking engagement with the inner peripheral circumferential wall of the body conduit assuring secure, locked, movement-free positioning by said medication delivery vehicle in the precisely desired position in said fluid carrying conduit.

4. The medication delivery vehicle defined in claim 3, wherein said vehicle is further defined as comprising
E. internal reservoirs for holding the desired medication; and
F. semi-permeable polymeric material for controlling the rate of diffusion of the medication to the desired site.

5. The medication delivery vehicle defined in claim 3, wherein said vehicle is formed from bioerodable material, thereby dissolving in the bodily fluid after the medication is dispensed.

6. A medication delivery vehicle insertable in an elongated, substantially continuous, open ended conduit in the human body through which fluid normally travels, said medication delivery vehicle comprising
A. a substantially continuous, thin-walled, elongated, hollow, tubular shaped member, peripherally surrounded and enveloped by said fluid carrying conduit of the human body, and having
   a. a first proximal edge comprising a generally rounded shape and defining a first portal zone
   b. a second distal edge comprising a generally rounded shape and defining a second portal zone,
   c. a substantially continuous, elongated length of thin-wall material
      1. extending between and interconnecting said proximal edge with said distal edge,
      2. comprising an outer peripheral surface and an inner peripheral surface, and a total thickness therebetween of between about 0.1 millimeters and 1 millimeter,
      3. defining an elongated substantially continuous fluid flow zone
         i. commencing at said first portal zone,
         ii. terminating at said second portal zone, and
         iii. peripherally surrounded and defined by said inner peripheral surface, and
      4. said outer surface, when inserted in the desired conduit, extending in juxtaposed, spaced, substantially aligned, peripherally enveloped relationship with the inner wall of said fluid carrying conduit, and having an elongated central axis extending substatnially coaxially with the central axis of the fluid carrying conduit,
thereby providing a non-interfereing, free flow-assuring medication delivery vehicle whereby the fluid normally passing through said body conduit freely flows through said fluid flow zone of said member, without experiencing any flow interference or flow reduction; and B. conduit engaging and anchoring means formed about the outer peripheral surface of said member and positioned for secure abutting and locking engagement with the inner peripheral wall of the body conduit, thereby assuring secure, locked movement free positioning of said delivery vehicle in the desired position in said fluid carrying conduit, whereby said delivery vehicle, once inserted in the desired conduit, is capable of delivering medication to the precisely desired site, without adversely affecting the flow through said conduit, while being in a secure, fixed, anchored position.

7. The medication delivery vehicle defined in claim 6, wherein said conduit-engaging and position-anchoring means is further defined as comprising at least one portion of the outer peripheral surface of the elongated member forming the medication delivery vehicle.

8. The medication delivery vehicle defined in claim 7, wherein said conduit-engaging and position-anchoring means is further defined as comprising the outer peripheral surface directly adjacent said first portal zone.

9. The medication delivery vehicle defined in claim 8, wherein said generally rounded first proximal edge is further defined as comprising a diameter greater than the diameter of the generally rounded second distal edge, forming a generally truncated, thin-walled, substantially continuous, elongated, hollow, tubular shaped medication delivery vehicle.

10. The medication delivery vehicle defined in claim 6, wherein said fluid carrying conduit is further defined as comprising blood carrying conduits such as arteries and veins.

* * * * *